United States Patent
Cereceda Balic

(10) Patent No.: US 11,714,048 B2
(45) Date of Patent: Aug. 1, 2023

(54) SYSTEM AND METHOD FOR BLACK CARBON (BC) MASS CONCENTRATION DETERMINATION IN SNOW SAMPLES AND SIMILAR MATRICES

(71) Applicant: UNIVERSIDAD TECNICA FEDERICO SANTA MARIA, Valparaiso (CL)

(72) Inventor: Francisco Javier Cereceda Balic, Qulpué (CL)

(73) Assignee: Universidad Tecnica Federico Santa Maria, Valparaiso (CL)

( * ) Notice: Subject to any disclaimer, the term of this patent is extended or adjusted under 35 U.S.C. 154(b) by 557 days.

(21) Appl. No.: 16/690,013

(22) Filed: Nov. 20, 2019

(65) Prior Publication Data
US 2021/0148818 A1    May 20, 2021

(51) Int. Cl.
*G01N 21/59* (2006.01)
*G01N 1/40* (2006.01)
*G01N 33/18* (2006.01)

(52) U.S. Cl.
CPC .......... *G01N 21/59* (2013.01); *G01N 1/4077* (2013.01); *G01N 33/1826* (2013.01); *G01N 2001/4088* (2013.01); *G01N 2033/1873* (2013.01)

(58) Field of Classification Search
CPC .. G01N 21/59; G01N 1/4077; G01N 33/1826; G01N 2001/4088; G01N 2033/1873; G01N 21/278; G01N 2001/2893
See application file for complete search history.

(56) References Cited

U.S. PATENT DOCUMENTS

2006/0080954 A1 * 4/2006 Bardasz .............. C10M 159/20
                                                         60/297
2019/0113431 A1 * 4/2019 Solomon ............. C09D 11/324

FOREIGN PATENT DOCUMENTS

| CN | 201277963 Y | * | 7/2009 | |
| CN | 109738243 A | * | 5/2019 | |
| CN | 112250055 A | * | 1/2021 | ............ C01B 32/05 |
| CN | 213623294 U | * | 7/2021 | ............ C01B 32/05 |
| WO | WO-2004096046 A1 | * | 11/2004 | ............ B01L 3/502 |

OTHER PUBLICATIONS

Reunión 2019 de Sociedad Chilena de la Criósfera: Libro de resúmenes, 82 pages (2019).
Cereceda-Balic et al., "Optical determination of black carbon mass concentrations in snow samples: a new analytical method," Science of the Total Environment, 697, 9 pages (Aug. 14, 2019).
Reunión 2019 de la Sociedad Chilena de la Criósfera: Libro de resúmenes, 82 pages (2019).

* cited by examiner

*Primary Examiner* — Marcus H Taningco
(74) *Attorney, Agent, or Firm* — Foley & Lardner LLP

(57) ABSTRACT

The present disclosure provides a filtration system for collecting Black Carbon (BC) samples present in snow samples and similar matrices which comprises the collection of BC in polycarbonate filters. It also discloses a method of determination of (BC) in snow samples and similar matrices using real soot from the gases of a diesel vehicle as calibration standards.

16 Claims, 2 Drawing Sheets

SYSTEM AND METHOD FOR BLACK CARBON (BC) MASS CONCENTRATION DETERMINATION IN SNOW SAMPLES AND SIMILAR MATRICES

FIELD OF THE INVENTION

The present invention is directed to the measurement of Black Carbon in snow samples and similar matrices. In particular, the present invention is directed to a filtration system for collecting Black Carbon samples from different matrices and the measurements of theses samples using real soot collected directly from diesel vehicle exhaust as a calibration standard.

BACKGROUND

Black carbon (BC) aerosols contain sub-micrometer diameter particulates emitted during incomplete combustion of carbonaceous fuels (or containing carbon, oxygen and hydrogen) including fossil fuels, bio-fuels, and biomass. BC is emitted from both anthropogenic and natural sources such as mobile sources, wildland fires, etc. Fuel type and combustion conditions affect BC concentration and, therefore, BC emission factors.

BC is one of the key species of atmospheric aerosols contributing to positive radiative forcing at the top of the atmosphere and negative radiative forcing at the surface level due to its strong light absorption heating the atmosphere and changing its radiative balance. BC aerosols remain in the atmosphere until they are removed by wet or dry deposition and due to their small particle size, they can travel thousands of kilometres from their source.

BC also can be deposited onto snow and ice surfaces, darkening the surface, lowering the surface albedo, accelerating the melting of snow and ice, due to the presence of these black particles (BC) that heat up due to the absorption of solar radiation in the infrared region. The final consequence of this process is an accelerated retreat of glaciers and the loss of white surfaces of the planet that increase the greenhouse effect and global climate change. To the above is added the modification of the albedo resulting from the change in the morphological characteristics of snow crystals or ice, which is called change in the grain, this may be due to the simple aging of snow with the passage of the time, even due to chemical modifications, such as the presence of BC, organic or inorganic chemical compounds deposited on snow and/or ice whose origin are mainly atmospheric aerosols.

Due to the impacts of BC deposition onto snow on regional and global climate forcing, a number of studies have been carried out analysing the reduction of snow albedo by deposition of aerosols of environmental BC in mountain areas such as the Himalayas (Jacobi et al., 2015; Ginot et al., 2015; Ming et al., 2008, 2009, 2013), Sierra Nevada (USA) (Lee and Liou, 2012; Sterle et al., 2013), Hokkaido island (Aoki et al., 2011), Alps (Oerlemans et al., 2009; Painter et al., 2013; Gabbi et al., 2015; Dumont et al., 2017; Sigl et al., 2018), and Andes Mountain (Portillo, Chile) (Cereceda-Balic et al., 2018), among others.

PRIOR ART DESCRIPTION

Measurement of BC mass concentrations in snow samples has been mainly carried out using optical methods and, in particular, employing commercial optical transmissometers, which commonly use quartz filters to filter BC and measure its optical attenuation. These devices are made for determining BC mass concentrations in the air (atmospheric soot), but they are not adapted or calibrated for determining BC mass concentrations in water or snow samples. Additionally, this type of devices are calibrated using materials that simulate BC particles, however, these alternative materials are not representative of BC particles that are mainly emitted from combustion processes in vehicles, boilers, heating systems using biomass, wildfires, etc.

Only scarce information is available about the calibration of the analytical methods used for the determination of BC in snow samples and about Quality Assurance and Quality Control (QA/QC) for these methods. One of the main reasons for this is the lack of a certified reference material for this type of analyte in the snow matrix and other liquid samples.

By way of example, the publication by Doherty et al. ("Observed vertical redistribution of black carbon and other insoluble light-absorbing particles in melting snow", JGR Atmospheres, 118, 2013, 5553-5569) refers to a study showing results from BC measurements in snow samples from Barrow (Alaska), the Dye-2 station in Greenland and Tromsø (Norway) during the melt season. The analysis of the snow samples comprises filtering and drying the samples, then analyzing them with a laboratory spectrophotometer to measure light absorption by insoluble particles (at a wavelength of 400-750 nm with a resolution of 10 nm). Measured absorption is converted to an equivalent BC mass on the filter by using a calibration curve based on a set of filters loaded with synthetic BC. However, it fails to specify the source of said synthetic material, the characteristics of the filter and the obtaining of these calibration filters.

The publication by Wendl et al. ("Optimized method for black carbon analysis in ice and snow using the Single Particle Soot Photometer (SP2)", Atmos. Meas. Tech., 7, 2667-2681, 2014) discloses a study aiming to optimize the method for measuring BC in snow and ice using a Single Particle Soot Photometer (SP2). It describes that different materials were tested for preparing calibration curves: Aquadag (water-based colloidal graphite coating) Aquablack 162, Cabojet 200 (ink), flame soot and fullerene soot. The samples are introduced into the photometer through a nebulizer. The obtained results showed that Aquablack, Carbojet and flame soot are not suitable for external calibration, since the SP2 photometer sensitivity is unknown for these materials. Instead, the SP2 sensitivity to Aquadag and fullerene soot is known, and its main mass is within the SP2 detection limits. However, calibration problems of the SP2 equipment related to the nebulization of the aqueous samples of synthetic BC when introduced into the measuring equipment, which cause irreproducibilities in the measurement, are mentioned.

On the other hand, several studies have been published about the use of Carbon Black, such as Monarch 71 (Cabot Corporation, U.S.A.) as standard material for determining BC. However, it should be noted that Monarch 71 is a soot surrogate of BC, free of organic components, and it is not a product generated by a real combustion process. Therefore, it has a different physicochemical structure, and therefore different optical properties than atmospheric soot. In previous studies, Monarch 71 has been used in increasing concentrations for method calibration without presenting the basic QA/QC parameters of the calibration curve, such as linearity, limit of detection (LOD), and limit of quantification (LOQ), making these methods low in analytical strictness.

Table 1 summarizes the methods described in the prior art for assessing BC mass concentrations in snow samples. For example, Gogoi et al., 2016, and Gogoi et al., 2018, used an optical method using the same Soot Scan equipment, model OT21, employing quartz fiber filters. However, in neither of these publications the analytical parameters of the method are mentioned, such as QA/QC, but they only describe the use of verification of the analysis using a neutral density photometric standard filter kit, which is the calibration set for the verification of the proper functioning of the Soot Scan equipment, model OT21, which is marketed by the manufacturer for his equipment, but is not a proper calibration method for evaluating the matrix effect or the analytical quality of the determination of BC in snow.

Other authors (Yang et al., 2015; Hadley et al., 2010; Zhang et al., 2017) used the thermo-optical method according to the IMPROVE A protocol for the measurement of BC in snow samples. However, these three publications also used quartz filters with their well-known limitations for effectively removing BC from liquid samples, like melted snow, due to quartz filters being only suitable for filtering low volumes of water, not having sharply defined pore sizes and undergoing physical modifications of their fibers when water is passed through the filter, which changes their optical properties.

In addition, they do not mention how the calibration was carried out or the type of BC standard used. Only Zhang et al. (2017) disclosed the precision of the method used, determined by carrying out triplicate analyses of samples, but not by a calibration curve using a "reference BC material" or similar, in order to evaluate the matrix effect and to obtain the analytical quality and the merit figures of the method for the BC determination.

Finally, Ming et al. (2009) used quartz filters and coulometric titration-based analyses (using the Strohlein Coulomat 702C® with detection limit of 3 µgC and precision of 0.02 µgC). In their method, they mention a previous combustion step of the filters to eliminate organic carbon (OC), which could cause a positive bias by the formation of additional, pyrolitic BC in the combustion process. Calibration and other QA/QC parameters were also not presented in this publication.

TABLE 1

Summary of literature methods for analysis of BC mass concentrations in snow samples

| Authors | Filter Type | Methodology | Calibration Material |
|---|---|---|---|
| Gogoi et al., 2018 | Quartz Fiber Filter | Optical Transmissometer Magee Scientific Soot Scan OT21 | Neutral density photometric standard filter kit |
| Gogoi et al., 2016 | Quartz Fiber Filter | Optical Transmissometer Magee Scientific Soot Scan OT21 | Neutral density photometric standard filter kit |
| Hadley et al., 2010 | Quartz Fiber Filter | Thermo-Optical Analysis (TOA) IMPROVE A | N/I |
| Zhang et al., 2017 | Quartz Fiber Filter | Thermo-Optical Analysis (TOA) IMPROVE A | N/I |
| Yang et al., 2015 | Quartz Fiber Filter | Thermo-Optical Analysis (TOA) IMPROVE A | N/I |
| Schwarz et al., 2012 | Polycarbonate filter 0.2 µm pore | Single Particle Soot Photometer (SP2) and Sphere/Integrating Sandwich Spectrophotometer (ISSW) | Fullerene Soot and Monarch 71 |
| Sterle et al., 2013 | No filter used | Single Particle Soot Photometer (SP2) | Aqua-Black 162 |
| Wendl et al., 2014 | No filter used | Single Particle Soot Photometer (SP2) | Aquadag, Aquablack 162, Cabojet 200, Fullerene soot and Flame soot |
| Clarke and Noone, 1985 | Polycarbonate filter 0.4 µm pore | Sphere/Integrating Sandwich Spectrophotometer (ISSW) | Monarch 71 |
| Doherty et al., 2010 | Polycarbonate filter 0.4 µm pore | Sphere/Integrating Sandwich Spectrophotometer (ISSW) | Monarch 71 |
| Wang et al., 2013 | Polycarbonate filter 0.4 µm pore | Sphere/Integrating Sandwich Spectrophotometer (ISSW) | Fullerene Soot |
| Clarke and Noone, 1985 | Polycarbonate filter 0.4 µm pore | Sphere/Integrating Sandwich Spectrophotometer (ISSW) | Monarch 71 |
| Ming et al., 2009 | Quartz fiber filter | Coulometric titration-based analysis | N/I |

N/I: Not Informed

In view of the difficulties and the scarce analytical information mentioned in the methods described above, the aim of the presently claimed invention is to provide a novel analytical method for the determination of Black Carbon mass concentrations in water and/or snow samples, or similar, through the use of a calibration curve prepared with a material that presents optical characteristics comparable to BC generated naturally in the combustion process and present in snow.

SUMMARY OF THE INVENTION

The presently claimed invention refers to a method for quantifying Black Carbon present in snow samples or similar matrices. Moreover, it provides a new material for use as calibration standard in said method. Finally, it provides a system that allows carrying out the quantitative analytical determination of said Black Carbon.

DETAILED DESCRIPTION

Figure 1:
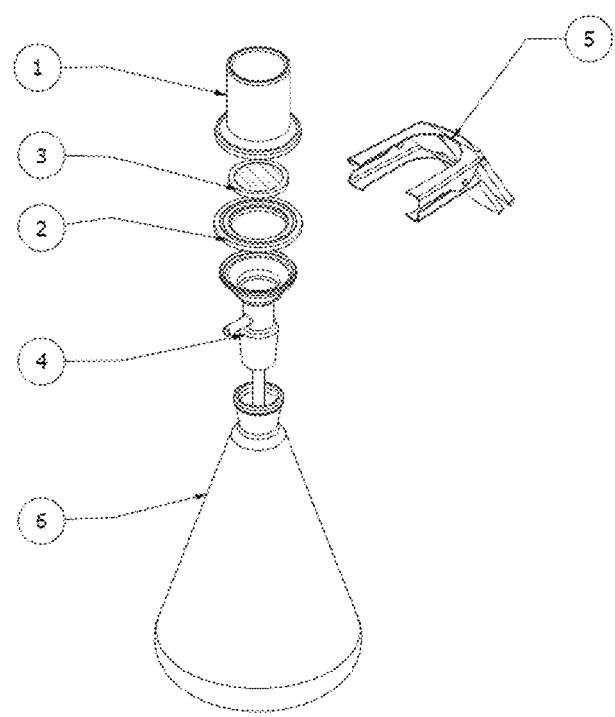
FIG. 1: Photography of the filtration system designed for collection of samples to be measured.

The method of the presently claimed invention comprises determining Black Carbon present in snow samples or similar, by measuring attenuation of polycarbonate filters used in a transmissometer. Furthermore, the calibration curve is prepared using as material real soot collected directly from diesel vehicle exhaust (SDVE), which is deposited onto polycarbonate filters.

In order to prepare the samples, a filtration system designed and manufactured for generating a homogenous BC circular exposure area of a defined diameter over the polycarbonate filter.

Characterization of the Samples and Calibration Standards

The presently claimed invention uses the filter-based absorption method to characterize light absorbing particles in snow. In particular, BC mass concentrations are measured using an optical transmissometer. This instrument can be used quickly and easily, in the field or in the laboratory, to determine optical attenuation and mass concentrations of the BC deposited on snow. The attenuation measurement is performed at a defined wavelength of 880 nm, and is a non-contaminating and non-destructive method, and it does not require support gases or consumables. The specific wavelength of 880 nm is for the determination of BC by scientific convention, and can be measured at any other wavelength to determine the other absorption capacities of other aerosols (impurities) present in snow or similar matrices.

Calibration Curve

The material used for calibration curve preparation is real soot collected directly from diesel vehicle exhaust (SDVE). Each calibration curve point corresponds to an increasing amount of the soot mentioned above (BC) which is suspended in an isopropanol and water mixture, both to avoid adherence of hydrophobic BC particles to the surfaces of the glassware and to eliminate the soluble organic carbon fraction present in the material to be calibrated, so that what is retained on the polycarbonate filter is only BC.

Preparation of Samples

The amount of snow sample that normally needs to be analyzed in order to determine a measurable BC concentration with optical methods like of this invention is around 500 to 1500 mL of liquid water (melted snow). In order to evaluate possible optical changes of the polycarbonate membrane of the filter, different water volumes were passed through this filter (i.e., 500, 1000, and 1500 mL), followed by measurement of optical light attenuation with the SootScan™, Model OT21; no difference in attenuation was observed between filters (see Table 2).

TABLE 2

Assessment of the optical changes in the polycarbonate membrane filters when passing different volumes of a water/isopropanol mixture 80/20% (v/v).

| 500 mL mixture IR ATN | 1,000 mL mixture IR ATN | 1,500 mL mixture IR ATN |
|---|---|---|
| 0 | 0 | 0 |
| 0 | 0 | 0 |
| −1 | 0 | 0 |
| −1 | 0 | 0 |
| 0 | 0 | 0 |

TABLE 2-continued

Assessment of the optical changes in the polycarbonate membrane filters when passing different volumes of a water/isopropanol mixture 80/20% (v/v).

| 500 mL mixture IR ATN | 1,000 mL mixture IR ATN | 1,500 mL mixture IR ATN |
|---|---|---|
| 0 | 0 | 0 |
| 0 | 0 | 0 |
| 0 | 0 | 0 |
| 0 | 0 | 0 |
| 0 | 0 | 0 |

ATN: Attenuation at a wavelength of 880 nm.

In order to obtain a circular exposure area of BC on the polycarbonate filter in a homogeneous manner and to measure it in the transmissometer, a filtration system as shown in FIG. 1 was designed and built.

The filtration system (FIG. 1) comprises a glass funnel with PTFE stopcock for filtration flow control; (1) a specially designed PTFE conical funnel to generate a circular exposure area of BC of about 2.5 cm in diameter on the polycarbonate filter(which depends on the device used); (2) a PTFE filter support with silicone O-ring and porous still frit; (3) a Nuclepore polycarbonate filter 47 mm in diameter with 0.4 μm diameter pores; (4) a connection funnel that allows to join the filtration system with the flask for the liquid reception that also has a connection for a vacuum pump; (5) a flask for the liquid reception; and (6) a metal clip to connect the filtration system to the connection funnel (4) in a hermetically sealed way. Filtration is done by applying vacuum. In the same way that the filters with the calibration material, which contain the samples are also washed with a mixture of isopropanol and water to remove any organic carbon that may be present. Finally, the samples thus prepared are dried at room temperature before being measured in the transmissometer.

The calibration blank were prepared by passing through a clean polycarbonate filter the same isopropanol/water mixture used for sample filtration, without the presence of calibration material, i.e. soot obtained from the exhaust of a diesel vehicle.

Black Carbon Measurement

The filters were analyzed using an Optical Transmissometer measures and compares the optical transmission between sample and reference filters at a wavelength of 880 nm for the measurement of BC mass. The instrument determines the attenuation ATN due to particles loaded onto the sample filter. The assumption behind this and other optically based methods is that attenuation through the filter is proportional to the BC mass loading on the filter (Hansen et al., 1984; Liousse et al., 1993; Petzold et al., 1997; Ahmed et al., 2009).

Also, in order to compare the behaviour of quartz filters (47-mm diameter, grade QM-A; Whatman, Darmstadt, Germany) using the OT-21 transmissometer to measure BC in snow samples, a blank quartz fiber filter was measured and a calibration curve was established according to this new analytical procedure development.

BC surface loading B (mass/area) on quartz fiber filters can be determined used by relating the filter attenuation ATN measured at a wavelength of 880 nm to B as:

$$ATN = \frac{100}{k}(1 - e^{-k\sigma B}), \tag{1a}$$

where k is the loading effect parameter, σ is the BC mass attenuation cross section, and ATN is defined as:

$$ATN = -100 \ln(I/I_0), \quad (1b)$$

where the factor of "100" is historically used for convenience, I and $I_0$ are the detector intensity signals for filters with and without aerosol deposition, respectively.

For small BC filter loadings (i.e., kσB<<1), the exponential function in eq. (1) can be approximated by the first two terms of its power series as:

$$e^{-k\sigma B} \cong 1 - k\sigma B, \quad (2a)$$

yielding a greatly simplified form of eq. (1a) as:

$$ATN \cong 100\sigma B, \quad (2b)$$

and allowing for calculation of surface loading B as:

$$B \cong \frac{ATN}{100 \, \sigma} \quad (2c)$$

The values of "BC with Magee Scientific algorithm" shown as function of "ATN IR" were calculated with a Magee Scientific spreadsheet that uses eq. (2c) with σ=16.6 m2/g for the determination of the surface loading B and the subsequent calculation of the total filter BC mass by multiplying B with the filter area A=π(d/2)2, with a filter diameter.

Preferred Embodiments

The present invention refers to a filtration system for collecting Black Carbon (BC) samples present in snow samples and similar matrices which comprises:

a conical funnel with PTFE stopcock for inlet of the liquid sample;

a PTFE filter support with silicone O-ring and porous still frit;

a polycarbonate filter or membrane;

a connection funnel that allows to join the filtration system with the flask for the reception of the liquid that furthermore has a connection for a vacuum pump;

a container for the reception of liquids; and a clip for connecting the filtration system to the connecting funnel in a hermetically sealed way.

In an embodiment of the invention the funnel is a specially designed PTFE funnel to generate a circular area of a homogenous BC accumulation on the polycarbonate filter or membrane.

At the same time, the present invention is directed to a method of determination of BC in snow samples and similar matrices, which comprises the steps of:

preparing snow samples by means of the filtration system according to claim 1 in order to obtain a polycarbonate filter with a circular area with the BC deposited;

preparing calibration standards with real soot from exhaust gases of a diesel vehicle at different concentrations on the polycarbonate filter or membrane;

measuring attenuation of filters containing the calibration standards, and obtaining the calibration curve with the equation of the curve and its QA/QC parameters;

measuring the attenuation of the real snow samples prepared in step i); and interpolating values of at least one sample in the calibration curve to obtain BC mass.

In this method the preparation of the samples and standards comprise the addition one or more solvents to minimize adherence of particles to the surfaces of the filtration system.

In a preferred embodiment, the added solvent is an isopropanol/water mixture. More preferred the isopropanol/water ratio is of 20/80% (v/v).

In an embodiment, the preparation of the calibration curve comprises obtaining at least two polycarbonate filters with increasing concentrations of BC per filter.

In some embodiments, the preparation of the calibration curve comprises obtaining at least six polycarbonate filters with increasing concentrations of BC per filter to obtain QA/QC parameters of the calibration curve and of this analytical method.

The method according to the invention comprises the measuring attenuation of polycarbonate filters is carried out using an Optical Transmissometer.

In a preferred embodiment, the attenuation measurement for each polycarbonate filter is made at a wavelength of 880 nm.

The method described further comprises preparing and determining a blank sample. In particular, the preparation of a blank sample comprises using the system according to claim 1 without any sample or BC and adding the same solvent(s) that were used to prepare the real snow samples and calibration standards.

Finally, the present invention provided herein a calibration standard for determining BC present in snow samples and similar matrices, which comprises real soot from exhaust gases of a diesel vehicle (SDVE), deposited onto a polycarbonate filter or membrane.

EXAMPLES

The amount of BC in snow samples from three different areas of the Chilean Andes Mountains was determined. The snow samples were collected at the end of winter, when precipitations and particulate matter deposition are minor, and when the snowpack reaches its maximum depth before the onset of spring snowmelt.

Sampling

The snow samples consisted of a 5-cm thick layer collected from the top of the snowpack. Sample sizes were around 1,000-1,500 g and snow samples were kept frozen at −20° C. until they could be processed.

All sampling material was washed with Extran® phosphate-free detergent and then rinsed with distilled water, followed by deionized water, and finally with ultrapure quality water.

Snow sampling were collected from three different locations. Those samples named M1 come from a place mainly affected by very diverse urban emissions of a city highly populated, located at 40 km; the second samples, named M2, come from an area with pollution levels similar to urban background areas dominated by wood burning emissions from domestic heating and cook stoves; and the third samples, M3, come from an area wherein the main pollution source is very intense traffic from vehicles, especially buses and heavy duty trucks.

Preparation of Samples

Frozen snow samples were deposited into clean glass beakers and melted in a microwave oven until it becomes liquid. It is important to minimize the melting time of the samples in the container to minimize losses of BC and other particles to the container walls.

During the melting process, the isopropanol samples were added (in proportion 20% v/v) to minimize adherence of particles to the surfaces of the filtration system.

In the filtration system (FIG. 1) a polycarbonate membrane filter (Nuclepore®, Whatman, Darmstadt, Germany), of 47 mm in diameter with 0.4 µm diameter pores, was used.

Upon passing the melted snow through the filtration system, a homogenous and circular exhibition area of BC of 2.5 in diameter was generated on the polycarbonate filter.

Vacuum pressure for filtration was 0.4-0.6 bar, which was generated with an oil-free vacuum pump, and provided with parts and pieces of Teflon free of contamination.

Once filtrated the samples, the filters were dried to then measure their attenuation in a SootScan™, Model OT21 Optical Transmissometer (Magee Scientific; Berkeley, Calif., USA).

The entire mass of soot was assumed to be BC, which is justified because the polar organic compounds that might have been present in the BC were dissolved in the isopropanol/water mixture.

Calibration Curve

The optical response of the Magee Soot Scan OT21 was calibrated by preparing a series of polycarbonate filters with increasing concentrations of SDVE to complete at least 6 different concentrations, between 0.17 to 4.51 mg of BC per filter.

The attenuation for each filter was measured using a predetermined fixed wavelength of 880 nm.

Table 3 shows the parameters QA/QC obtained from the calibration curve.

deposited onto polycarbonate filters and its analytical characteristics (LOD, LOQ) for quantitative BC determination.

Both the limit of detection (LOD) and the limit of quantification (LOQ) were determined by 10 measurements of the blank filter (n=10), which was prepared by passing 500 ml of isopropanol/water mixture in the proportion of 20/80% (v/v) through the filtration system, without the presence of calibration material, i.e. soot obtained from the exhaust of a diesel vehicle.

The method reproducibility was evaluated with real ambient snow samples, particularly M3, considering a n=10, obtaining a relative standard deviation value of 1.15%.

TABLE 4

Reproducibility results of the method using real samples of snow (M3) M3

| IR ATN | Mass (mg) | Volume (L = kg) | Concentration (µg kg-1) |
|---|---|---|---|
| 46 | 1.640 | 0.450 | 3,645.500 |
| 46 | 1.640 | 0.450 | 3,645.500 |
| 46 | 1.640 | 0.450 | 3,645.500 |
| 45 | 1.604 | 0.450 | 3,565.140 |
| 45 | 1.604 | 0.450 | 3,565.140 |
| 46 | 1.640 | 0.450 | 3,645.500 |
| 45 | 1.604 | 0.450 | 3,565.140 |
| 46 | 1.640 | 0.450 | 3,645.500 |
| 45 | 1.604 | 0.450 | 3,565.140 |
| 46 | 1.640 | 0.450 | 3,645.500 |

Determination of BC in Snow Samples

Table 5 shows the mean mass concentrations±standard deviations (at µg of BC kg-1 of snow) of the samples from locations M1, M2 and M3, for each of them, each measurement was made in triplicate.

TABLE 5

BC mass concentration in real ambient snow samples from three sampling sites determined the new analytical method described here

| Sample Area | Attenuation | BC Mass (mg) | Sample Volume (L) | BC Mass Concentration (µg of BC kg-1 of snow) |
|---|---|---|---|---|
| M1 (1) | 5 ± 1 | 0.172 ± 0.019 | 1.140 | 151.010 ± 16.383 |
| M1 (2) | 62 ± 1 | 2.205 ± 0.030 | 1.170 | 1,884.360 ± 26.067 |
| M1 (3) | 71 ± 1 | 2.545 ± 0.024 | 0.425 | 5,987.448 ± 56.732 |
| M2 (1) | 120 ± 1 | 4.302 ± 0.019 | 1.490 | 2,887.484 ± 12.534 |
| M2 (2) | 6 ± 1 | 0.179 ± 0.019 | 0.760 | 236.033 ± 24.574 |
| M2 (3) | 124 ± 1 | 4.447 ± 0.025 | 0.960 | 4,632.309 ± 26.341 |
| M3 (1) | 14 ± 1 | 0.491 ± 0.015 | 0.680 | 721.200 ± 22.425 |
| M3 (2) | 30 ± 1 | 1.065 ± 0.011 | 0.553 | 1,926.693 ± 20.681 |
| M3 (3) | 50 ± 2 | 1.789 ± 0.075 | 0.422 | 4,238.835 ± 178.175 |

TABLE 3

Parameters QA/QC obtained from the calibration curve

| Ecuación de regresión | Coeficiente de correlation ($r^2$) | Rango lineal (mg) | Error estandar (Sy/x) | LOD (mg) | LOQ (mg) |
|---|---|---|---|---|---|
| y = 27.65x + 0.64 | 0.995 | 0.036-4.510 | 3.21 | 0.011 | 0.036 |

Figure 2:
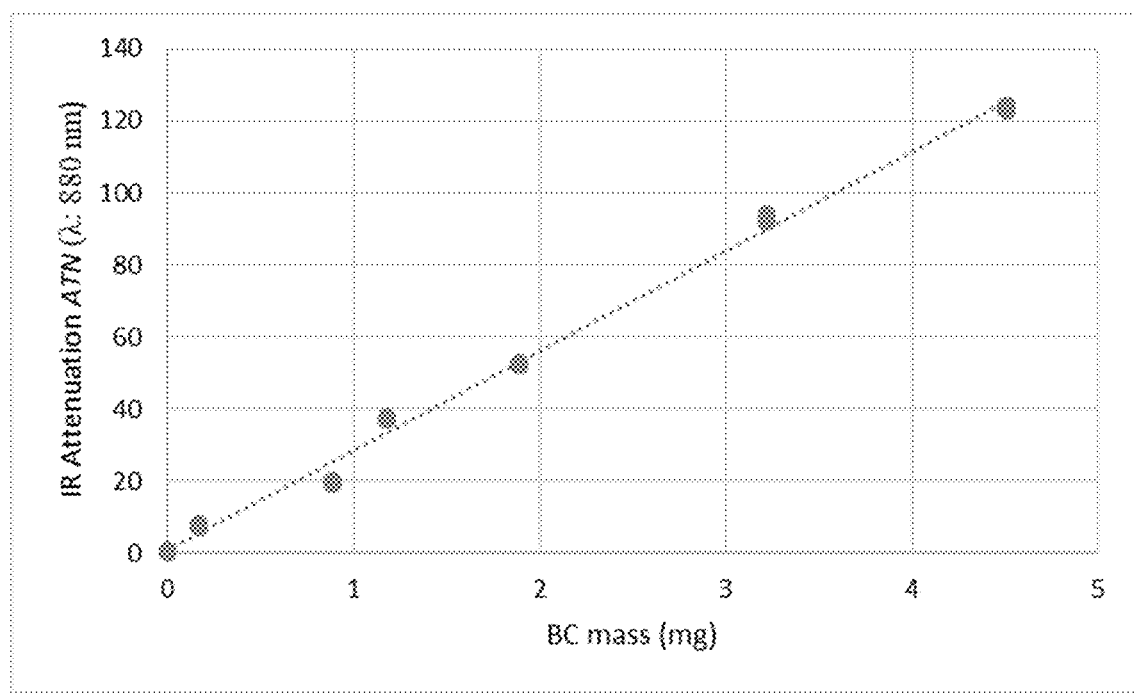
FIG. 2: Graph showing the calibration curve of the example according to the invention.

FIG. 2 shows the calibration curve obtained with the values in Table 2, where the optical filter attenuation at a wavelength of 880 nm is shown as function of BC mass In the place where the M1 samples were obtained, the atmosphere can be influenced by the complex urban emissions, especially because of the prevailing winds in the area that carry these contaminants from the city to the Andes mountain range. BC mass concentrations obtained in surface snow of this sampling site ranged from 151 to 5.987 µg kg-1, including the highest BC mass concentration observed among the nine samples from the three locations studied. This may be due to the transport of urban pollution, which presents a significant enrichment for a variety of trace element markers, related to traffic, smelting, and biomass burning, pollutant sources that also cause BC emissions.

On the other hand, M2 samples were collected from about 60 km of a settlement where the main BC source is biomass burning, BC mass concentrations observed in surface snow of this sampling site ranged from 236 to 4.632m kg-1.

As can be seen from these data, BC mass concentrations observed in location M3 in surface snow, ranged from 721 to 4.239 μg kg-1. In the place where M3 samples come from the main BC sources are diesel engines (light and heavy vehicles), therefore, BC deposited in the snow of said place is heavily influenced by the sources of vehicular traffic between the border of Chile and Argentina.

Calibration Methods Using Quartz Filters (Comparative)

Given the prevalence of prior art works using quartz filters for the collection of atmospheric samples, the method according to the invention was compared using instead of polycarbonate filters, quartz filters for the collection and measurement of BC samples in snow, using the same SootScan™ device, Model OT21.

Increasing concentrations of the same SDVE and similar procedure to those used in the previous example were prepared but using quartz filters (see Table 6).

TABLE 6

Calibration curve using quartz filters

| Mass (mg) | Attenuation ATN IR ($\lambda$: 880 nm) |
|---|---|
| 0 | 6 |
| 0.722 | 71 |
| 0.936 | 162 |
| 1.824 | 134 |
| 2.468 | 186 |
| 4.234 | 124 |

For the preparation of the blank, a water/isopropanol mixture (80/20 v/v) was passed through a quartz microfiber filter with a diameter of 47 mm (grade QM-A; Whatman, Darmstadt, Germany), as described in the publications cited above.

Figure 3:
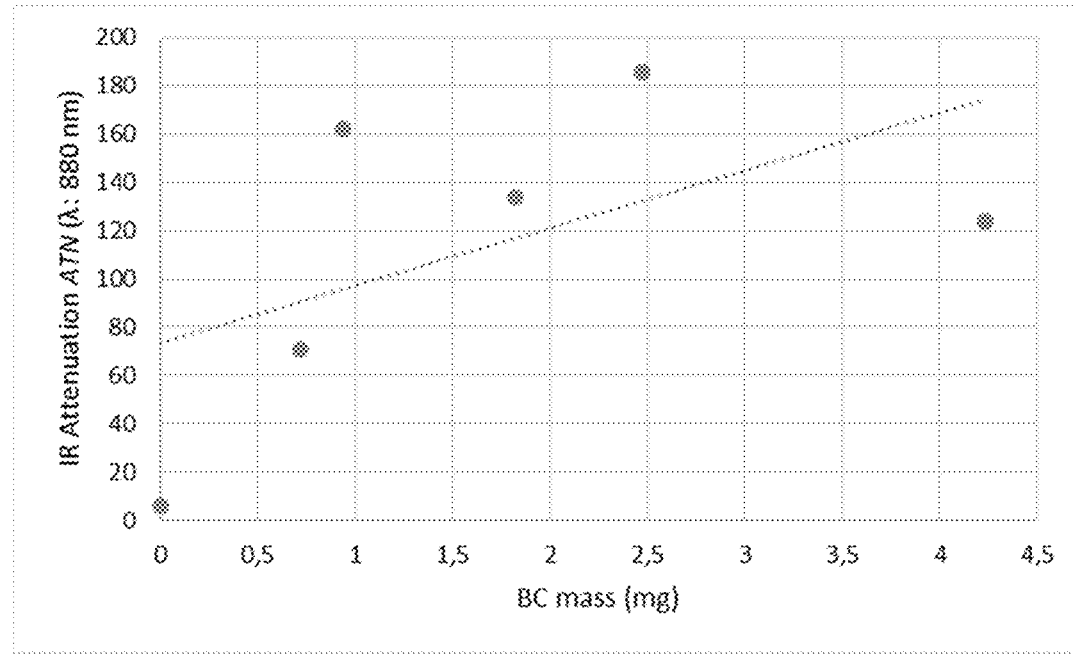
FIG. 3: Graph showing the calibration curve of the comparative example.

FIG. 3 shows the calibration curve for Magee Soot Scan OT21 showing optical filter attenuation at a wavelength of 880 nm as function of BC mass deposited onto quartz filters and its analytical characteristics (i.e., LOD, LOQ) for quantitative BC determination.

Table 7 shows the analytical parameters obtained.

TABLE 7

Parameters QA/QC obtained from the calibration curve

| Equation of regression | Correlation coefficient (r2) | Linear range (mg) | Standard error (Sy/x) | LOD (mg) | LOQ (mg) |
|---|---|---|---|---|---|
| y = 23.82x + 73.42 | 0.302 | 0.217-4.232 | 50.89 | 0.027 | 0.217 |

The calibration curve using the quartz filters showed analytical parameters very different to those obtained with the polycarbonate filters of the presently claimed invention. All analytical merit figures of the method using quartz filters demonstrate that this method is not appropriate for the quantitative determination of BC in snow samples.

While the quartz filter for the blank sample showed an attenuation of 6 units at 880 nm, the polycarbonate filter showed an attenuation of 0 units.

Despite the low analytical quality of the calibration curve obtained using quartz filters, the algorithm of the OT-21 transmissometer was used directly and without any modification to obtain the BC mass present in the snow samples (mg of BC per kg of snow), as some authors do, using quartz filters or other types of filters to measure BC in snow samples.

Figure 4:
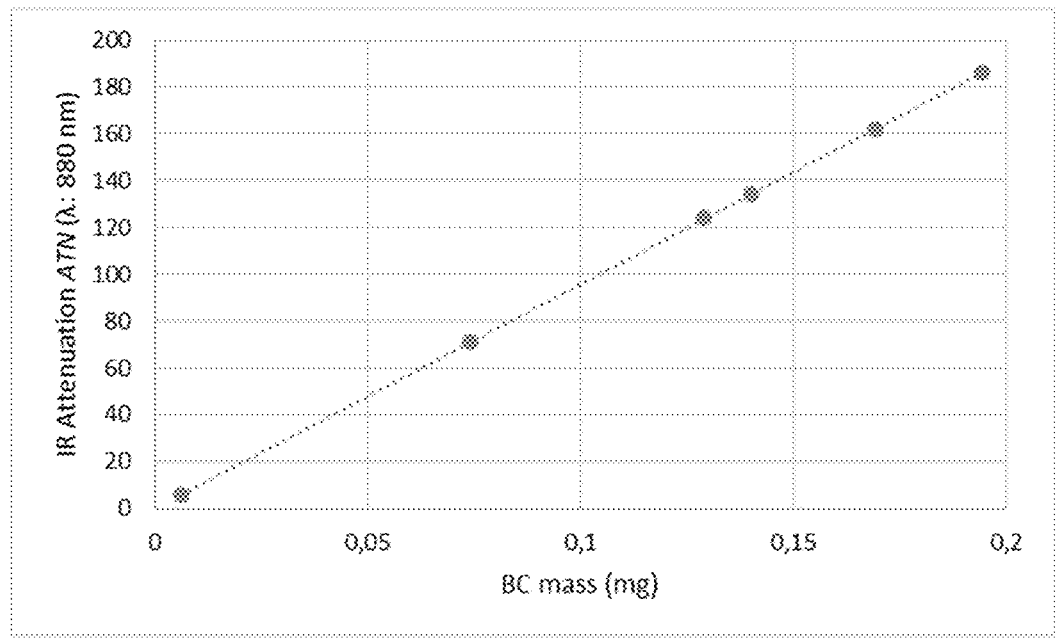
FIG. 4: Graph showing the calibration curve obtained from the transmissometer equipment OT-21 at 880 nm.

FIG. 4 shows the calibration curve for Magee Soot Scan OT21 showing optical filter attenuation at a wavelength of 880 nm as function of BC mass deposited onto quartz filters obtained with the transformation algorithm of the Magee Soot Scan OT21 and its analytical characteristics (i.e., LOD, LOQ) for quantitative BC determination.

The calibration curve showed excellent analytical parameters, as shown in Table 8. However, the comparison of the BC mass obtained by using the quartz filters with BC deposited to the BC mass used by the transformation algorithm produced very different results (see Table 9).

TABLE 8

Parameters QA/QC obtained from the calibration curve

| Equation of regression | Correlation coefficient ($r^2$) | Linear range (mg) | Standard error (Sy/x) | LOD (mg) | LOQ (mg) |
|---|---|---|---|---|---|
| y = 958.62x − 0.04 | 1.000 | 0.005-0.194 | 0.22 | 0.001 | 0.005 |

TABLE 9

Comparison of BC mass obtained through weighing BC mass of quartz filters and using transformation algorithm of OT-21 transmissometer

| Mass (mg) | Attenuation ATN IR ($\lambda$: 880 nm) | Total Mass (mg) BC with Magee | % decreasing |
|---|---|---|---|
| 0 | 6 | 0.006 | — |
| 0.722 | 71 | 0.074 | 90 |
| 0.936 | 162 | 0.169 | 82 |
| 1.824 | 134 | 0.140 | 92 |
| 2.468 | 186 | 0.194 | 92 |
| 4.234 | 124 | 0.129 | 97 |

By determining BC mass concentrations in snow samples using quartz filters by direct transformation of the OT-21 transmitter algorithm (which is designed for use in quartz filters, but with atmospheric BC samples), it is possible to observe an underestimate of BC concentration in snow samples ranging from 82 to 97%.

Conclusions

Using as a reference material for the development of a new method for the determination of BC the real soot collected directly from diesel vehicle exhaust (SDVE), as reference material allows obtaining a multipoint calibration curve for BC concentration levels usually found in snow and similar matrices.

The good analytical results obtained for the calibration curve using SDVE as calibration standards allow its comparative use with snow samples due to the similarity in its optical properties with BC, that is, with insoluble organic components that are comparable to each other.

Another advantage of this technique is that the measurement of the absorption of light by particles is closely related to the actual absorption of solar radiation in the snow and that the processing and filtering of the sample can be carried out in situ, directly under conditions of field, even in remote locations.

The design and development of a filtration system especially suitable for generating a homogeneous and circular BC accumulation zone on a polycarbonate filter that exactly corresponds to the filter exposure zone when exposed to the optical pass of the instrument used for BC measurements, allows for less BC loss during the filtration process, greater measurement effectiveness and greater measurement reproducibility.

The proposed method allows the removal of the polar organic part from both the reference material (SDVE) and the BC samples, thanks to its aqueous treatment and the addition of the isopropanol/water (V/V) mixture, which also minimizes the loss of BC through adhesion on the walls of the glass containers and the filtration system.

It is important to emphasize that to carry out the method of the present invention can be used any type of optical instrument to measure BC that is available in the market, allowing to determine the amount of BC present in matrices such as snow, ice, melt water, rivers, among others.

The previous section is considered only illustrative of the principles of the invention. The scope of the claims should not be limited by the exemplary embodiments described in the previous section, but should be given the broadest interpretation consistent with the description as a whole.

The invention claimed is:

1. A filtration system for collecting Black Carbon (BC) samples present in snow samples and similar matrices, the filtration system comprising:
   a conical funnel with PTFE stopcock for inlet of the liquid sample;
   a PTFE filter support with silicone o-ring and porous still frit;
   a polycarbonate filter or membrane;
   a container for the reception of liquids;
   a connection funnel that allows to join the conical funnel, the PTFE filter support and the polycarbonate filter or membrane to the container for the reception of the liquid and that furthermore has a connection for a vacuum pump; and
   a clip for connecting the conical funnel, the PTFE filter support and the polycarbonate filter or membrane to the connecting funnel.

2. The filtration system according to claim 1, wherein the conical funnel is a specially designed PTFE funnel to generate a homogeneous and circular area of BC accumulation on the polycarbonate filter or membrane.

3. The filtration system according to claim 2, wherein the circular area of BC accumulation is equal to or greater than 10 mm in diameter.

4. The filtration system according to claim 2, wherein the circular area of BC accumulation is 25 mm.

5. Method of determination of Black Carbon (BC) in snow samples and similar matrices, the method comprising:
   i) preparing snow samples by means of the filtration system according to claim 1 in order to obtain a polycarbonate filter or membrane with a homogeneous and circular area with the BC deposited;
   ii) preparing calibration standards with real soot from exhaust gases of a diesel vehicle at different concentrations on one or more further polycarbonate filter or membrane;
   iii) measuring attenuation of the one or more further polycarbonate filter or membrane containing the calibration standards, and obtaining a calibration curve with the equation of the curve and its QA/QC parameters;
   iv) measuring the attenuation of the real snow samples prepared in step i); and
   v) interpolating values of at least one sample in the calibration curve to obtain BC mass.

6. The method according to claim 5, wherein the preparation of the samples and standards comprise the addition one or more solvents to minimize adherence of particles to the surfaces of the filtration system.

7. The method according to claim 6, wherein the added solvent is an isopropanol/water mixture.

8. The method according to claim 7, wherein the isopropanol/water ratio is of 20/80% (v/v).

9. The method according to claim 5, wherein the preparation of the calibration curve comprises obtaining at least two polycarbonate filters with increasing concentrations of BC per filter.

10. The method according to claim 9, wherein the preparation of the calibration curve comprises obtaining at least six polycarbonate filters with increasing concentrations of BC per filter to obtain QA/QC parameters of the calibration curve.

11. The method according to claim 5, wherein the measuring attenuation of polycarbonate filters is carried out using an Optical Transmissometer.

12. The method according to claim 11, wherein the attenuation measurement for each polycarbonate filter is made at a wavelength suitable for the absorption of aerosols present in snow or similar matrices, wherein the preferred wavelength is 880 nm.

13. The method according to claim 5, further comprising preparing and measuring a blank sample.

14. The method according to claim 13, wherein the preparation of the samples and standards comprise the addition one or more solvents to minimize adherence of particles to the surfaces of the filtration system; and
   wherein the preparation of a blank sample comprises obtaining a third polycarbonate filter prepared without any sample or BC and adding the same solvent(s) used to prepare the real snow samples and calibration standards.

15. The method according to claim 13, wherein the measurement of the said blank sample comprises an attenuation measurement at a same wavelength as the attenuation measurement of the samples.

16. A calibration standard for determining Black Carbon present in snow samples and similar matrices, the calibration standard comprising real soot from exhaust gases of a diesel vehicle, deposited on a polycarbonate filter or membrane, wherein said real soot is suspended in one or more solvents to minimize adherence of particles to the surfaces of the filtration system and to eliminate a soluble organic carbon fraction present in the real soot.

* * * * *